(12) United States Patent
Howes, Jr. et al.

(10) Patent No.: US 8,082,764 B2
(45) Date of Patent: Dec. 27, 2011

(54) WASHING MACHINE WITH A TITRATION INDICATOR BASED ON MEASUREMENTS OF SOLUTION CONDUCTIVITY

(75) Inventors: Ronald B. Howes, Jr., Minneapolis, MN (US); Robert E. May, Lakeville, MN (US); David Howland, Aptos, CA (US)

(73) Assignee: Ecolab Inc., St. Paul, MN (US)

( * ) Notice: Subject to any disclaimer, the term of this patent is extended or adjusted under 35 U.S.C. 154(b) by 57 days.

(21) Appl. No.: 12/506,589

(22) Filed: Jul. 21, 2009

(65) Prior Publication Data

US 2009/0283112 A1 Nov. 19, 2009

Related U.S. Application Data

(62) Division of application No. 10/328,497, filed on Dec. 23, 2002, now Pat. No. 7,584,762.

(51) Int. Cl.
*D06F 33/00* (2006.01)

(52) U.S. Cl. ............ 68/12.27; 68/12.02; 68/12.18; 68/207

(58) Field of Classification Search .......... 68/12.02, 68/12.18, 12.27, 207; 222/56
See application file for complete search history.

(56) References Cited

U.S. PATENT DOCUMENTS

| | | |
|---|---|---|
| 3,774,056 A | 11/1973 | Sample et al. |
| 4,241,400 A | 12/1980 | Kiefer |
| 4,509,543 A | 4/1985 | Livingston et al. |
| 4,733,798 A | 3/1988 | Brady et al. |
| 4,756,321 A | 7/1988 | Livingston et al. |
| 5,014,211 A | 5/1991 | Turner et al. |
| 5,038,807 A | 8/1991 | Bailey et al. |
| 5,404,893 A | 4/1995 | Brady et al. |
| 5,556,478 A | 9/1996 | Brady et al. |
| 5,625,908 A | 5/1997 | Shaw |
| 5,956,487 A | 9/1999 | Venkatraman et al. |
| 6,003,070 A | 12/1999 | Frantz |
| 6,133,555 A | 10/2000 | Brenn |
| 6,357,292 B1 | 3/2002 | Schultz et al. |
| 6,494,961 B2 | 12/2002 | Simpson |
| 2001/0039501 A1 | 11/2001 | Crevel et al. |
| 2001/0047214 A1 | 11/2001 | Cocking et al. |
| 2001/0053939 A1 | 12/2001 | Crevel et al. |
| 2001/0054038 A1 | 12/2001 | Crevel et al. |

OTHER PUBLICATIONS

Transmittal of the PCT international Search Report mailed Jun. 30, 2004 for counterpart application No PCT/US2003/37010, 7 pages.

*Primary Examiner* — Yelena G Gakh
(74) *Attorney, Agent, or Firm* — Shumaker & Sieffert, P.A.

(57) ABSTRACT

A system and method is disclosed for indicating satisfactory times for titrating a chemical solution, e.g., cleaning product, used by a utility device to clean and/or sanitize various types of articles. The utility device is described in an exemplary embodiment as being a warewashing machine that applies the chemical solution to articles provided to the machine on racks. The chemical solution is formed in a solution tank from a combination of at least one chemical product and at least one rinse agent. Whereas the chemical product is described as a detergent, the rinse agent is described as water. Over a time period including multiple wash cycles, the chemical product and the rinse agent are added to the solution tank, thereby changing conductivity of the chemical solution. The present invention senses various types of information associated with the formation of the chemical solution and applies one or more test conditions to the sensed information to determine satisfactory time periods for measuring concentration of the chemical product relative to the chemical solution. Indications of the occurrence of these satisfactory times are presented on a display module in a manner visible to field persons responsible for titrating the chemical solution.

15 Claims, 5 Drawing Sheets

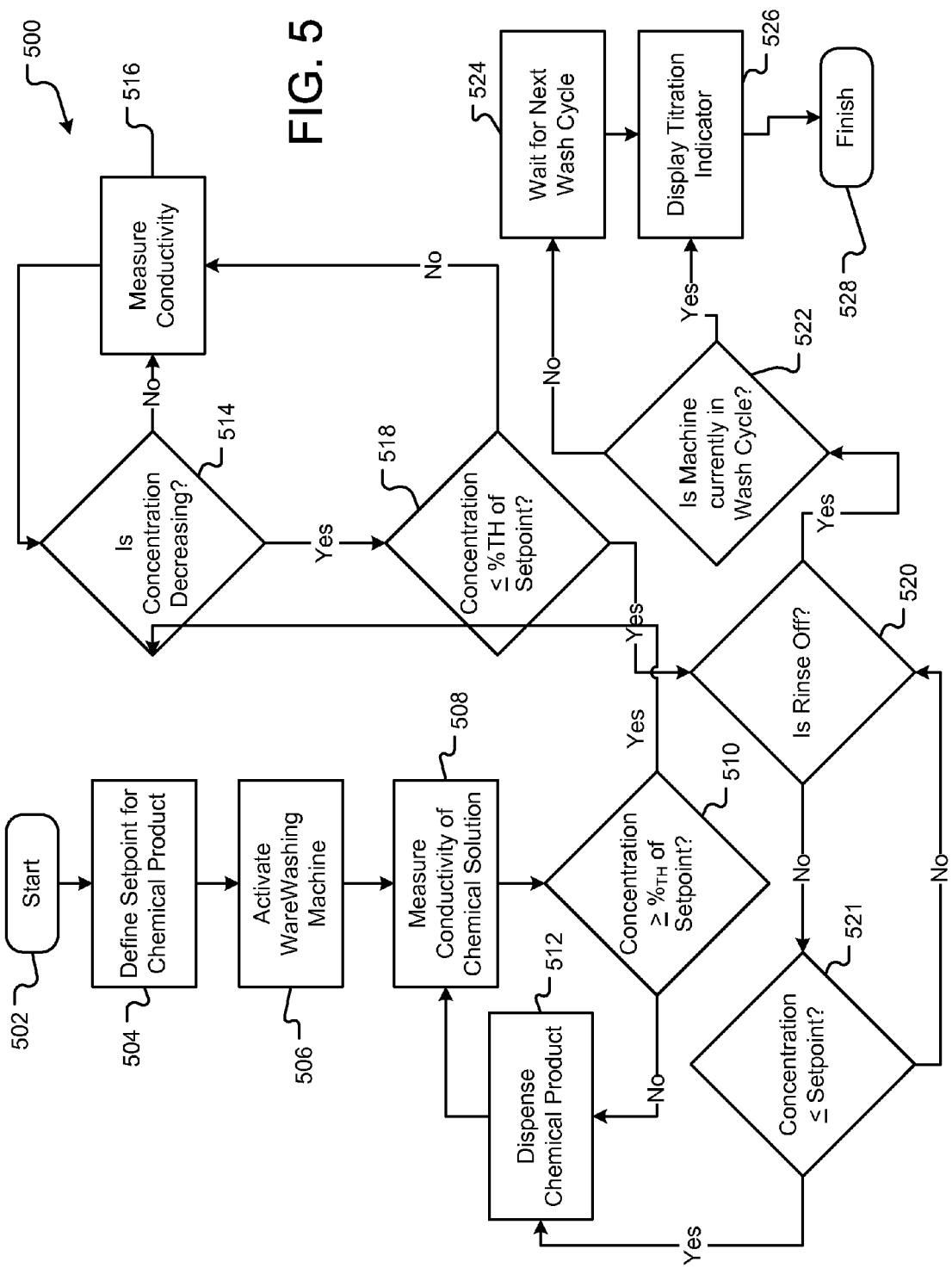

WASHING MACHINE WITH A TITRATION INDICATOR BASED ON MEASUREMENTS OF SOLUTION CONDUCTIVITY

CROSS-REFERENCED TO RELATED APPLICATIONS

This application is a Divisional Application of U.S. application Ser. No. 10/328,497 filed Dec. 23, 2002, the entire content of which is incorporated herein by reference.

TECHNICAL FIELD

The invention relates generally to a utility device, and more particularly to measuring conductivity of a chemical solution associated with the utility device.

BACKGROUND OF THE INVENTION

A warewashing machine is a utility dishwasher used in many restaurants, healthcare facilities and other locations to efficiently clean and sanitize cooking and eating articles, such as, dishes, pots, pans, utensils and other cooking equipment. Articles are placed on a rack and provided to a washing chamber of the warewashing machine. In the chamber, rinse agents, e.g., water, and cleaning products, e.g., chemical solutions containing detergents and soaps, are applied to the articles over a predefined period of time referred to as a "wash cycle." A wash cycle includes a cleaning cycle and a rinsing cycle. At least one cleaning product is applied to the articles during the cleaning cycle. At least one rinse agent is applied to the articles during the rinsing cycle. The article racks contain holes that enable the chemical product and rinse agent to pass through racks during the cleaning and rinsing cycles, respectively. At the end of the wash cycle, the rack is removed from the washing chamber so that other racks carrying other articles may be moved into the washing chamber. The wash cycle is then repeated for each of these subsequent racks. Wash cycles may be customized for specific types of racks and the articles that the racks carry.

The cleaning products applied to the articles by the warewashing machine are formed and contained in a solution tank typically located on the underside of the warewashing machine. A wash module is provided above the solution tank and in the lower portion of the washing chamber. The wash module extracts a cleaning product from the tank and applies the cleaning product to the articles contained in the rack during the cleaning cycle. Following the cleaning cycle, a rinse module, which is provided in the upper portion of the washing chamber, administers the rinsing cycle by applying a rinse agent to the articles thereby rinsing the cleaning product from the articles.

Conductivity of the cleaning products used by warewashing machines to clean and sanitize articles used in public facilities is governed by various food and health regulations. Conductivity is defined herein as a percent relation of chemical products forming a particular cleaning product. The term chemical product is used broadly to encompass, without limitation, any type of detergent, soap and rinse agent, including water. To meet these regulations, a conventional warewashing machine typically utilizes conductivity cells to sense conductivity of a cleaning product situated in the solution tank of the machine. This sensed information is provided to a controller overseeing operations of the warewashing machine. The controller uses this sensed information to determine the percent concentration of each chemical product forming the cleaning product. If the percent concentration of a particular chemical product is below a range prescribed by the governing regulations, the controller controls dispensing of an appropriate volume of that chemical product needed to force the conductivity of the cleaning product to the prescribed range.

As noted in the previous paragraph, conductivity cells provide a manner in which conductivity of a cleaning product can be controlled to meet certain regulations. However, these cells may yield inaccurate results or be altogether inoperable. For this reason, field persons responsible for operations of a warewashing machine are still required to periodically visit the machine to titrate the cleaning product used by the machine. The act of titrating a cleaning product refers to measuring conductivity of the cleaning product, and more particular, measuring a percent concentration of one or more chemical products forming the cleaning product.

In titrating a cleaning product, a field person first activates the warewashing machine to start a set of sequential wash cycles. Next, after waiting a predetermined period of time, the field person extracts a sample of the cleaning product from the solution tank. Then, using a conventional titration test kit, the field person estimates the conductivity of the cleaning product by applying one or more test chemicals to the sample and monitoring changes in the sample.

During sequential wash cycles, at least one chemical product and a rinse agent are added to the solution tank on demand thereby rendering continuous changes in the conductivity level of the cleaning product. That is, the percent concentration of the chemical product relative to the cleaning product varies as both chemical product and rinse agent are added to the solution tank. Depending on whether the field person extracts the cleaning product sample following dispensing of the rinse agent or the chemical product, the results of the titration may lack precision with respect to one another, thereby rendering the titration test relatively inaccurate. As such, the field person is required to estimate satisfactory times for titrating a cleaning product. The results of such titration tests therefore depend on how well the field person estimates such times and whether the warewashing machine is actually operating in a manner foreseeable by the field person when making the estimates. For at least these reasons, current titration techniques used by field persons are somewhat unreliable for ensuring that the cleaning products used by warewashing machines meet the various governing regulations.

SUMMARY OF THE INVENTION

In accordance with the present invention, the above and other problems are solved by a system and method for indicating satisfactory times for titrating a chemical solution associated with a utility device. The chemical solution is contained in a solution tank of the utility device and dispensed from the solution tank for application to various articles that the utility device is responsible for cleaning and/or sanitizing. In an embodiment, at least one chemical product and a rinse agent are added to the solution tank on demand thereby rendering continuous changes in the conductivity of the chemical solution. The present invention applies one or more test conditions to sensed information associated with formation of the chemical solution in the solution tank. During each time period wherein the one or more test conditions are satisfied, the present invention displays one or more titration indicators to indicate that the current time period is satisfactory for titrating the solution. During these satisfactory time periods, the percent concentration of the chemical product relative to the chemical solution may be measured to render an accurate reflection of the conductivity of the chemical solution as it is applied to the various articles.

In accordance with an embodiment, a setpoint value is defined for the chemical product. The setpoint value relates to a desired concentration level of the chemical product relative to the chemical solution. In this embodiment, one of the test conditions may be whether the current percent concentration of the chemical product relative to the chemical solution is less than a predetermined threshold percentage of the setpoint value. For example, if the current percent concentration is less than 103% of the setpoint value, the titration indicator is displayed to indicate a satisfactory time for titrating, assuming all other test conditions, if any, are satisfied.

In another embodiment, the utility device applies both the chemical solution and the rinse agent to the various articles during a wash cycle. Another test condition may be whether the rinse agent is currently being dispensed, i.e., applied directly to the various articles. If the rinse agent is not currently being dispensed, the titration indicator is displayed to indicate a satisfactory time for titrating, assuming all other test conditions, if any, are satisfied. Yet another test condition may be whether the chemical product is currently being added to the chemical solution. With respect to this test condition, the titration indicator is displayed to indicate a satisfactory time for titrating if the chemical product is not currently being dispensed, assuming all other test conditions, if any, are satisfied. Various other test conditions that may be applied to various types of sensed information for determination as to a satisfactory time for titrating a chemical solution are described and illustrated herein with respect to exemplary embodiments of the present invention. However, the present invention is not limited solely to those test conditions disclosed herein.

In accordance with an embodiment of the present invention, the utility device includes a wash module, a rinse module and the solution tank. The wash module pulls the chemical solution from the solution tank and applies the solution to the various articles. The rinse module applies the rinse agent to the various articles. Once applied to the articles, both the rinse agent and the chemical product flow into the solution tank.

In accordance with yet another embodiment, operations of the utility device are controlled and monitored by a control box. In this embodiment, the control box senses various types of information associated with the formation of the chemical solution in the solution tank as well as utilization of the solution by the utility device. Also in this embodiment, the control box applies the one or more test conditions to the sensed information to determine satisfactory times for titrating the chemical solution. For example, the control box monitors and controls operation of the wash module and the rinse module. By monitoring operation of the wash and the rinse module, the control box may determine whether the rinse agent or the chemical solution are currently being dispensed. The control box may also control and monitor a product reservoir storing the chemical product to determine whether the chemical product is being dispensed into the tank. Additionally, the control box receives sensed information related to the conductivity of the chemical solution from a sensor located within the solution tank. This sensed information may be used by the control box not only for determining a satisfactory time for titrating the chemical solution, but also for controlling the product reservoir to dispense a given volume of chemical product to the solution tank to increase percent concentration of the chemical product relative to the chemical solution. Upon determining that each of the applied one or more test conditions are satisfied, the control box displays the titration indicator to indicate satisfactory times for titrating the chemical solution.

In an embodiment of the present invention, the utility device is a warewashing machine wherein the various articles cleaned and/or sanitized by the machine are provided to the machine in article racks. The warewashing machine performs a wash cycle for each article rack wherein both the chemical solution and the rinse agent are applied to the articles contained in each rack. In this embodiment, the titration indicator is displayed on a display module, e.g., light-emitting diode or graphical user interface, of the control box.

The invention may be implemented as a computer process, a computing system or as an article of manufacture such as a solid state, non-volatile memory device or a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process.

These and various other features as well as advantages, which characterize the present invention, will be apparent from a reading of the following detailed description and a review of the associated drawings.

BRIEF DESCRIPTION OF THE DRAWINGS

FIG. 5 is a flow diagram that illustrates operational characteristics shown in FIG. 3 in more detail in accordance with an embodiment of the present invention.

DETAILED DESCRIPTION

Figure 1:
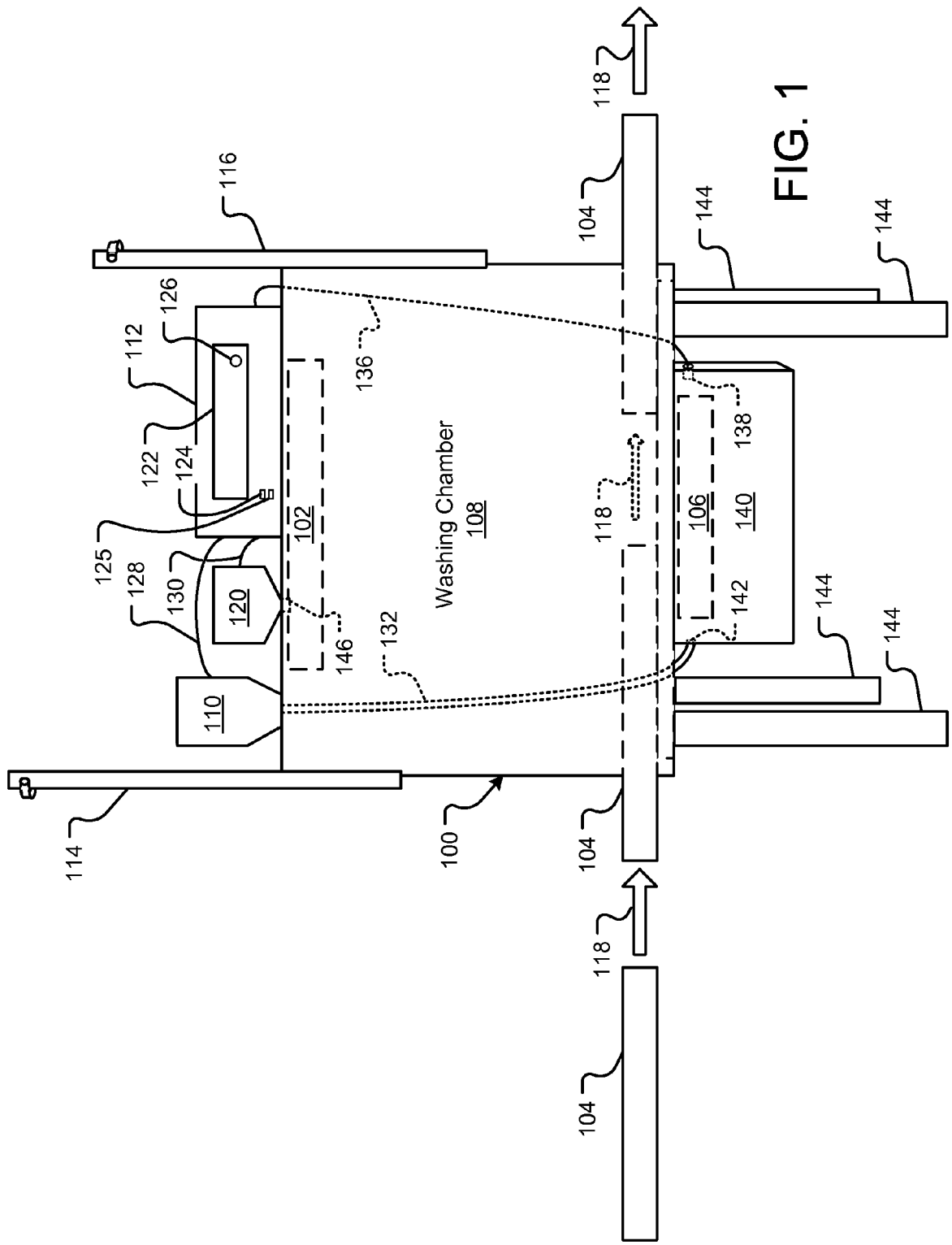
FIG. 1 illustrates components of a utility device in accordance with an embodiment of the present invention.

The present invention and its various embodiments are described in detail below with reference to the figures. When referring to the figures, like structures and elements shown throughout are indicated with like reference numerals. Objects depicted in the figures that are covered by another object, as well as the reference annotations thereto, are shown using dashed lines.

The present invention provides a method and system for indicating an optimal time for titrating a chemical solution to measure a concentration level of a chemical product forming the chemical solution. Such an optimal time is broadly defined herein as a being a time period wherein various conditions associated with formulation and/or conductivity of the chemical solution are most favorable, or at least satisfactory, for titrating the solution. In an embodiment of the invention, the chemical solution is a cleaning product used by a utility device to clean and/or sanitize objects placed in or around the device. The chemical solution is defined herein as a combination of a chemical product with other chemical products and/or water. In accordance with this embodiment, the utility device is described below as being a cleaning apparatus, and more particularly a commercial dishwasher, which is also referred to as a "warewashing machine." It should be appreciated, however, that the utility device may be any type of apparatus that prepares, formulates, allocates or otherwise utilizes a chemical solution to perform a task.

Referring now to FIG. 1, a warewashing machine 100 is shown in accordance with an embodiment of the present invention. The warewashing machine 100 is used to clean all types of dishware and kitchen objects, such as, without limitation, pots and pans used in restaurants, cafeterias and bakeries. Objects washed by the warewashing machine 100 are hereinafter referred to as "articles." The articles are provided to the warewashing machine 100 on article racks 104. The warewashing machine 100 may be a commercial dump or fill-type dish machine with standard article racks 104, although other cleaning apparatuses may be employed, including, without limitation, animal cage washers used in animal research areas.

The warewashing machine 100 includes a washing chamber 108, which, in the embodiment shown is enclosed by an entry sliding door 114 and an exit sliding door 116. The washing chamber 108 is supported above ground level by a plurality of legs 144. In operation, each article rack 104 carries one or more articles to be washed by the warewashing machine 100 into the washing chamber 108 through an opened entry sliding door 114. Arrows 118, which are provided in FIG. 1 for illustration purposes only, show the direction of article racks 104 through the washing chamber 108 in accordance with an embodiment of the present invention. Once an article rack 104 is located inside the washing chamber 108, the entry sliding door 114 and the exit sliding door 116 are both closed to fully contain the washing chamber 108 on all sides.

A rinse module 102 is provided within or directly above the washing chamber 108 for applying a rinse agent to articles placed in the article racks 104. Although water is hereinafter described as the exemplary rinse agent, it should be appreciated that other rinse agents may be applied to the articles by the rinse module 102. A wash module 106 is provided within or directly below the washing chamber 108 for applying a chemical solution to articles placed in the racks 104. The chemical solution cleans and sanitizes the articles for subsequent use in eating, cooking or otherwise utilizing. In an embodiment, the rinse module 102 and the wash module 106 include arms (not shown) operably mounted to a spindle (not shown) for rotation about the spindle axis. The arms of the rinse module 102 include a plurality of openings (not shown) through which water is passed to articles placed in the washing chamber 108. Likewise, the arms of the wash module 106 include a plurality of openings (not shown) through which the chemical solution is passed to articles placed in the washing chamber 108.

The chemical solution is formed and stored in a solution tank 140 positioned underneath the washing chamber 108. The chemical solution is formed as a combination of water provided by the rinse module 102 and one or more chemical products. For illustration purposes, and not by means of limitation, the chemical solution formed in the solution tank 140 is a combination of a single chemical product and water. Prior to being provided to the solution tank 140, the chemical product used to form the chemical solution is stored in a product reservoir 110 in either a solid or liquid form. If the chemical product is stored as a solid, water is applied to the product to liquefy the chemical product such that the product may provided to the solution tank 140 by way of a supply hose 132. Water is stored in a water reservoir 120 and dispensed into the washing chamber 108 by the rinse module 102. Water passes from the water reservoir 120 to the rinse module 102 by way of a coupling 146 therebetween. The rinse module 102 then applies the water to articles contained in a rack 104 situated in the washing chamber 108. An opening (not shown) is provided between the solution tank 140 and the washing chamber 108 to allow water provided to the washing chamber 108 to enter the solution tank 140. Water provided to the washing chamber 108 by the rinse module 102 passes through the opening into the solution tank 140, therein combining with pre-existing chemical solution to further dilute the chemical solution and therefore lower the concentration of chemical product in the solution.

In an embodiment of the present invention, operations of the warewashing machine 100 are controlled by a control box 112. In this embodiment, the control box 112 includes a control module (internal to the control box 112) and one or more display devices or modules, such as, without limitation, first and second status indicators, e.g., light emitting diodes (LED's), 124 and 125 and a graphical user interface 122. The control module performs operations stored as firmware or software to control and monitor various tasks administered by the warewashing machine 100 over a given wash cycle. For example, without limitation, the control module controls initiation of a wash cycle for each rack 104 provided to the warewashing machine 100, dispensing of the chemical product to the solution tank 140, initiation and operation of the wash module 106, and initiation and operation of the rinse module 102. The control module also measures conductivity of the chemical solution resident in the solution tank 140, and based on this measurement, controls the amount of chemical product dispensed to the solution tank 140. Furthermore, the control module generates information for display on the graphical user interface 122 as well as first and second status indicators 124 and 125 based on the various tasks that the control box 112 controls and monitors. In a preferred embodiment, the control module is a special-purpose controller manufactured by NOVA Controls. However, it should be appreciated that the control module may be any type or make of controller known to those skilled in the art.

The control module administers the aforementioned control and monitoring operations using a chemical product output control line 128, a water output control line 130 and a conductivity input control line 136, each input to the control box 112. The chemical product output control line 128 couples the control box 112 to a processor (not shown) responsible for dispensing the chemical product from the product reservoir 110. Under direction of the control module, the control box 112 transmits signals to the product reservoir processor over the chemical product output control line 128. These signals direct the product reservoir processor to dispense a particular volume of chemical product to the solution tank 140. If the chemical product is stored in the product reservoir 110 in a solid form, the product reservoir processor activates a water pump that applies a predetermined volume or water to the solidified chemical product. Upon the application of this predetermined volume of water, a predetermined volume of the chemical product in a liquid form is created and dispensed out of the product reservoir 110.

The water output control line 130 couples the control box 112 to a processor (not shown) responsible for dispensing water from the water reservoir 120. In an embodiment, the water reservoir processor controls operation of a water pump (not shown) that pushes water through an output of the water reservoir 120 and into the rinse module 102. Under direction of the control module, the control box 112 transmits signals to the water reservoir processor over the water output control line 130. These signals direct the water reservoir processor to activate the water pump to dispense a predetermined volume of water to the rinse module 102. Almost simultaneously and under the direction of the control module, the control box 112 also directs the rinse module 102 to provide the water to the washing chamber 108 for application to articles contained in an article rack 104 currently situated therein. The water passes over the articles and to the solution tank 140, where the water combines with chemical solution already contained in the tank 140, thereby diluting the solution.

As the chemical solution resides in the solution tank 140, the control module monitors concentration of the chemical product relative to the chemical solution. To accomplish this, the conductivity input control line 136 couples the control box 112 to one or more conductivity cells 138 that sense information related to concentration of the chemical product relative to the chemical solution. This sensed information, which is provided to the control box 112 over the conductivity input control line 136, is used by the control module to calculate percent (%) concentration of the chemical product relative to the chemical solution. Such conductivity cells and the method for determining % concentration are well known in the art and not described in further detail herein. For example, U.S. Pat. No. 4,733,798, which is incorporated by reference into this application, teaches both conventional electrode-bearing conductivity cells and electrode-less conductivity cells as well as measuring and controlling concentration of a chemical solution.

In accordance with an embodiment, the control box 112 is also coupled to the rinse module 102 and the wash module 106 by way of communication links (not shown). Under direction of the control module, the control box 112 controls operation of the rinse module 102 and the wash module 106 by issuing command signals to a processor (not shown) locally controlling the rinse module 102 and a processor (not shown) locally controlling the wash module 106. The command signals are transmitted to the processor over the aforementioned communication links. Based on such control, the control module can determine when either the wash module 106 or the rinse module 102 are currently active, and therefore dispensing the chemical solution or water, respectively.

In an embodiment, the first and second status indicators 124 and 125 indicate the current operation of the warewashing machine 100. For example, the first status indicator 124 may indicate to users that the warewashing machine 100 is currently activated and in the middle of a wash cycle. The second status indicator 125 may indicate to users that the warewashing machine 100 is not only activated, but that the chemical product is currently being dispensed to the solution tank 140. It should be appreciated that the status indicators 124 and 125 may be used for any other purpose related to operating characteristics of the warewashing machine 100. For example, in an alternative embodiment, the first and second status indicators 124 and 125 may be used as titration indicators.

Like the status indicators 124 and 125, the graphical user interface 122 is used for presenting information to a user of the warewashing machine 100. However, with the graphical user interface 122, the amount of information that may be presented to a user is substantially greater than the information that may be presented by the status indicators 124 and 125. For instance, the graphical user interface 122 may present to a user a selection screen that enables the user to define or modify a setpoint value for conductivity of the chemical solution. The setpoint value for conductivity is defined herein as a user-defined % concentration for a chemical product relative to the chemical solution formed in the solution tank 140. Such functionality may be desired because different chemical products are typically associated with different set point values for solutions formed in the solution tank 140. The selection screen may also enable a user to define the amount of time for a wash cycle, the amount of time that the wash module 106 is active and the amount of time that the rinse module 102 is active. Various other parameters and operating conditions may be defined or selected by a user through the graphical user interface 122 including, without limitation, a temperature for the rinse water, a rate in which conductivity is sensed, or monitored, by the one or more conductivity cells 138, a rate in which a chemical product is dispensed if the warewashing operations are time-based, e.g., in implementations where the control box 112 does not control dispensing based on information sensed by the one or more conductivity cells 138, a rate in which water is dispensed and velocity of the revolution of wash and rinse arms about a spindle axis. In addition, the graphical user interface 122 may be used limit operating access of the warewashing machine 100 to authorized users.

In an embodiment, the control module of the control box 112 determines, based on a set of predetermined test conditions, optimal times in which to measure % concentration of a particular chemical product relative to the chemical solution residing in the solution tank 140. The set of predetermined test conditions are related to various tasks, e.g., washing, rinsing, detected conductivity of the chemical solution, etc., administered by the warewashing machine 100. Such a process is described in greater detail below with reference to FIGS. 3, 4 and 5. The control module generates and displays on the graphical user interface 122 a titration icon 126 at time(s) during one or more wash cycles when it is optimal to measure % concentration of the chemical product relative to the chemical solution.

Although the titration icon 126 is described herein as being an exemplary titration indicator, other operator perceptible indicia may be used to indicate optimal times for titration. For instance, audio messages or other sounds, as well as tactile indicators, may be used as titration indicators. Furthermore, the status indicators 124 and 125 may be used as titration indicators. Even further, a textual message displayed on a liquid crystal display (LCD) may be used to indicate an optimal time for titrating. For instance, the textual message may read, "Titrate now!" The LCD may be included as part of the GUI 122 or a separate display module on the control box 112.

Operation of the warewashing machine 100 commences after both the entry sliding door 114 and the exit sliding door 116 are closed with a rack 104 being located substantially underneath the rinse module 102 and substantially above the wash module 106. Initially, the chemical solution is applied to the articles by the wash module 106 under direction of the control module of the control box 112. Application of the chemical solution to the articles is maintained for a predetermined period in time, as determined by the control module. After the chemical solution 106 is applied to the articles, the control module controls the rinse module 102 to apply water to the articles for rinsing the chemical solution away from the articles. Like the wash module 106, the rinse module 102 is operated for a predetermined period in time, as determined by the control module. After rinsing, the wash cycle is complete and the exit sliding door 116 is opened such that the rack 104 may be removed from the washing chamber 108 to make the warewashing machine 100 available for use by subsequent article racks 104.

Figure 2:
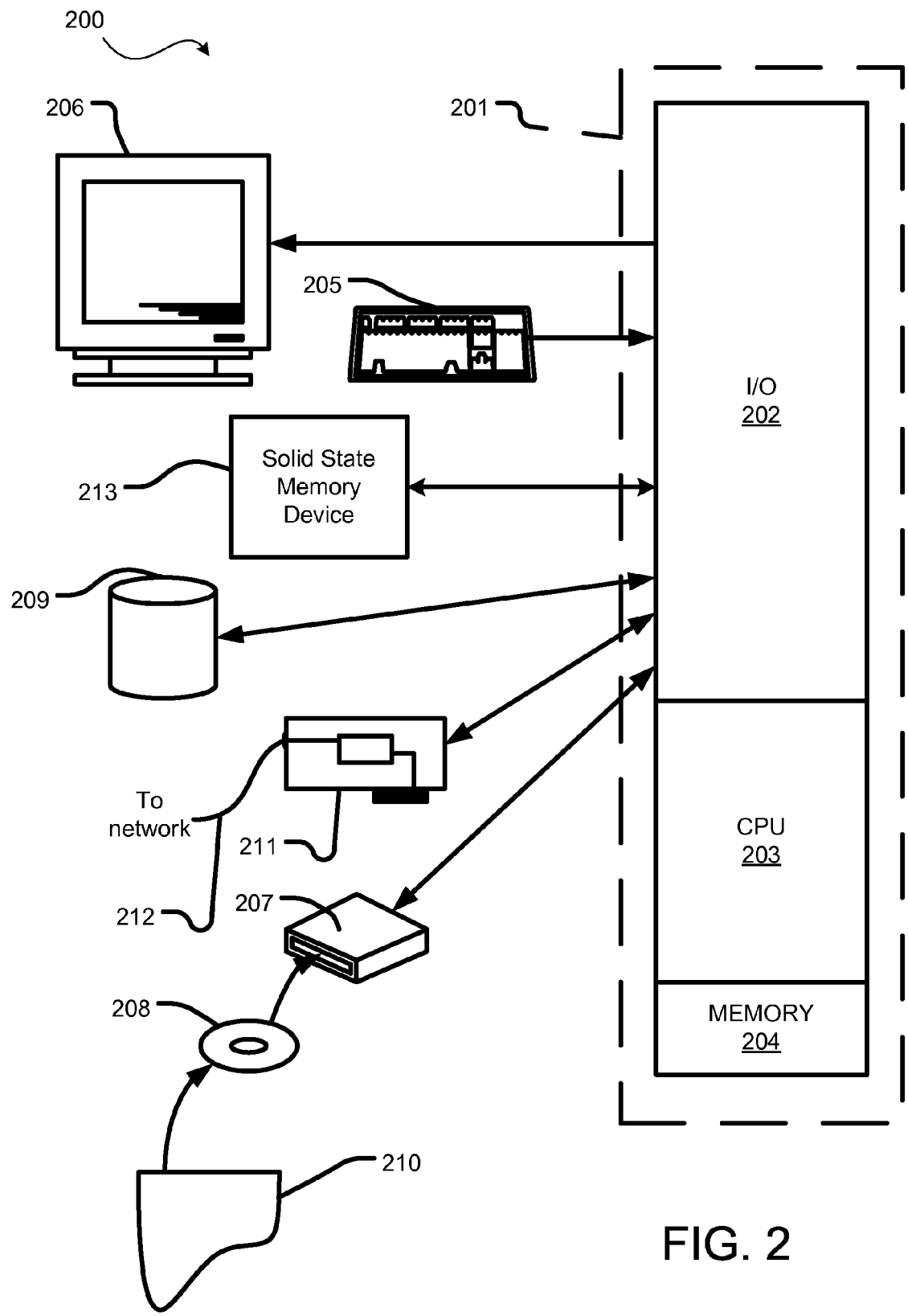
FIG. 2 depicts a general-purpose computer that implements logical operations of an embodiment of the present invention.

FIG. 2 depicts a computing system 200 capable of executing a program product embodiment of the present invention. One operating environment in which the present invention is potentially useful encompasses the computing system 200, such as, for example, the control box 112 or a remote computer to which information collected by the control box 112 may be uploaded. In such a system, data and program files may be input to the computing system 200, which reads the files and executes the programs therein. Some of the elements of a computing system 200 are shown in FIG. 2 wherein a control module, illustrated as a processor 201, is shown having an input/output (I/O) section 202, a microprocessor, or Central Processing Unit (CPU) 203, and a memory section 204. The present invention is optionally implemented in software or firmware modules loaded in memory 204 and/or stored on a solid state, non-volatile memory device 213, a configured CD-ROM 208 or a disk storage unit 209. As such, the computing system 200 is used as a "special-purpose" machine for implementing the present invention.

The I/O section 202 is connected to a user input module 205, e.g., a keyboard, a display unit 206 and one or more program storage devices, such as, without limitation, the solid state, non-volatile memory device 213, the disk storage unit 209, and the disk drive unit 207. The user input module 205 is shown as a keyboard, but may also be any other type of apparatus for inputting commands into the processor 201. The solid state, non-volatile memory device 213 is an embedded memory device for storing instructions and commands in a form readable by the CPU 203. In accordance with various embodiments, the solid state, non-volatile memory device 213 may be Read-Only Memory (ROM), an Erasable Programmable ROM (EPROM), Electrically-Erasable Programmable ROM (EEPROM), a Flash Memory or a Programmable ROM, or any other form of solid state, non-volatile memory. In accordance with one embodiment, the disk drive unit 207 is a CD-ROM driver unit capable of reading the CD-ROM medium 208, which typically contains programs 210 and data. Computer program products containing mechanisms to effectuate the systems and methods in accordance with the present invention may reside in the memory section 204, the solid state, non-volatile memory device 213, the disk storage unit 209 or the CD-ROM medium 208.

In accordance with an alternative embodiment, the disk drive unit 207 may be replaced or supplemented by a floppy drive unit, a tape drive unit, or other storage medium drive unit. A network adapter 211 is capable of connecting the computing system 200 to a network of remote computers via a network link 212. Examples of such systems include SPARC systems offered by Sun Microsystems, Inc., personal computers offered by IBM Corporation and by other manufacturers of IBM-compatible personal computers, and other systems running a UNIX-based or other operating system. A remote computer may be a desktop computer, a server, a router, a network PC (personal computer), a peer device or other common network node, and typically includes many or all of the elements described above relative to the computing system 200. Logical connections may include a local area network (LAN) or a wide area network (WAN). Such networking environments are commonplace in offices, enterprise-wide computer networks, intranets, and the Internet.

In accordance with a program product embodiment of the present invention, software instructions stored on the solid state, non-volatile memory device 213, the disk storage unit 209, or the CD-ROM 208 are executed by the CPU. In this embodiment, these instructions may be directed toward communicating data between a client and a server, detecting product usage data, analyzing data, and generating reports. Data, such as products usage data, corporate data, and supplemental data generated from product usage data or input from other sources, may be stored in memory section 204, or on the solid state, non-volatile memory device 213, the disk storage unit 209, the disk drive unit 207 or other storage medium units coupled to the system 200.

In accordance with one embodiment, the computing system 200 further comprises an operating system and usually one or more application programs. Such an embodiment is familiar to those of ordinary skill in the art. The operating system comprises a set of programs that control operations of the computing system 200 and allocation of resources. The set of programs, inclusive of certain utility programs, also provide a graphical user interface to the user. An application program is software that runs on top of the operating system software and uses computer resources made available through the operating system to perform application specific tasks desired by the user. In accordance with an embodiment, the operating system employs a graphical user interface 122 wherein the display output of an application program is presented in a rectangular area on the screen of the display device 206. The operating system is operable to multitask, i.e., execute computing tasks in multiple threads, and thus may be any of the following: Microsoft Corporation's "WINDOWS 95," "WINDOWS CE," "WINDOWS 98," "WINDOWS 2000" or "WINDOWS NT" operating systems, IBM's OS/2 WARP, Apple's MACINTOSH SYSTEM 8 operating system, X-windows, etc.

In accordance with the practices of persons skilled in the art of computer programming, the present invention is described below with reference to acts and symbolic representations of operations that are performed by the computing system 200, i.e., the control box 112 or a remote computer, unless indicated otherwise. Such acts and operations are sometimes referred to as being computer-executed. It will be appreciated that the acts and symbolically represented operations include the manipulations by the CPU 203 of electrical signals representing data bits causing a transformation or reduction of the electrical signal representation, and the maintenance of data bits at memory locations in the memory 204, the solid state, non-volatile memory device 213, the configured CD-ROM 208 or the storage unit 209 to thereby reconfigure or otherwise alter the operation of the computing system 200, as well as other processing signals. The memory locations where data bits are maintained are physical locations that have particular electrical, magnetic, or optical properties corresponding to the data bits.

The logical operations of the various embodiments of the present invention are implemented either manually and/or (1) as a sequence of computer-implemented steps running on a computing system, e.g., control box 112, and/or (2) as interconnected machine modules within the computing system. The implementation is a matter of choice dependent on the performance requirements of the computing system implementing the invention. Accordingly, the logical operations making up the embodiments of the present invention described herein are referred to alternatively as operations, acts, steps or modules. It will be recognized by one skilled in the art that these operations, structural devices, acts and modules may be implemented in software, in firmware, in special purpose digital logic, and any combination thereof without deviating from the spirit and scope of the present invention as recited within the claims attached hereto.

Figure 3:
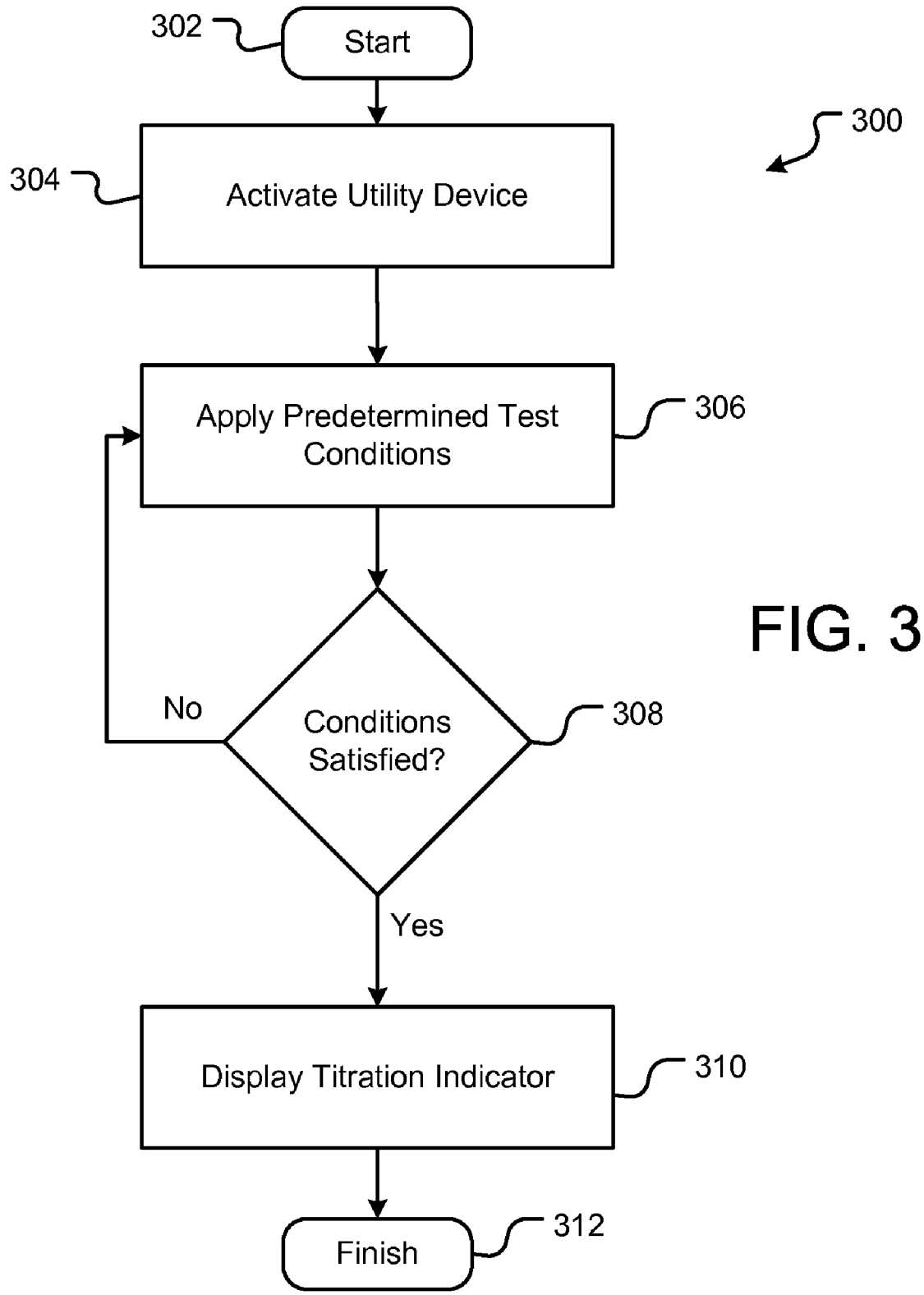
FIG. 3 is a flow diagram that illustrates operational characteristics for indicating a time period for measuring percent concentration of a chemical product relative to a chemical solution in accordance with an embodiment of the present invention.

With the computing environment in mind, FIG. 3 illustrates operational characteristics of a process 300 for indicating an optimal time for measuring conductivity of a chemical solution in accordance with an embodiment of the present invention. That is, the indication process 300 indicates a time period during which conductivity of a chemical solution may be measured to reflect an accurate measurement of percent (%) concentration of a chemical product in the solution. As shown and described in FIG. 1, the chemical solution is formed and contained in a solution tank 140 of a utility device 100. Operations of the utility device 100 are controlled and monitored by a control box 112 having a control module (not shown) and one or more display devices or modules, e.g., status indicators 124 and 125 and a graphical user interface 122. In an embodiment of FIG. 1, the indication process 300 is performed by the control module of the control box 112.

The utility device 100 is shown and described in FIG. 1 as a warewashing machine 100 in accordance with an exemplary embodiment of the present invention. Continuing with this exemplary embodiment, the indication process 300 is described below as a chemical solution is being formed and utilized by a warewashing machine 100 to clean and sanitize articles contained in an article rack 104. However, it should be appreciated that the present invention is not limited to application of warewashing machines 100, but rather the utility device may be any type of apparatus that prepares, formulates, allocates or otherwise utilizes a chemical solution to perform a task.

The indication process 300 is performed using an operation flow beginning with a start operation 302 and concluding with a terminate operation 312. Although a single iteration of the indication process 300 is shown and described in FIG. 3, the indication process 300 is sequentially performed as part of a continuous process in which a plurality of optimal time periods for measuring conductivity of the chemical solution are indicated in accordance with an embodiment of the invention. Such a continuous indication process is shown and described in more detail with reference to FIG. 4.

The start operation 302 is initiated as the warewashing machine 100 is activated to apply warewashing processes to one or more article racks 104 being provided to the washing chamber 108. Each instance that a rack 104 is provided to the washing chamber 108 constitutes a "wash cycle." The start operation 302 is initiated as the warewashing machine 100 is turned on to await the occurrence of an initial wash cycle. The occurrence of each wash cycle is detected as both the entry sliding door 114 and the exit sliding door 116 are closed to contain the washing chamber 108 on all sides. At such a detection of the initial wash cycle, the operation flow passes to an activate operation 304.

The activate operation 304 initiates warewashing processes, which include, without limitation, applying a chemical solution to articles placed on racks 104 provided to the washing chamber 108 and applying water or other rinse agents to the racks 104 following the application of chemical solution. Once initiated, the warewashing processes are performed for multiple wash cycles being applied to multiple article racks 104. After the warewashing machine 100 has activated warewashing processes, the operation flow passes to an application operation 306.

The application operation 306 applies one or more predetermined test conditions to the ware wash operating environment, which is broadly defined to encompass, without limitation, any and all operations of the warewashing machine 100, the chemical solution formed and stored in the solution tank 140 of the machine 100, and the chemical product(s), including rinse agents, used to form the chemical solution. The one or more predetermined test conditions are used by the control module of the control box 112 to determine an optimal time during which % concentration of a particular chemical product relative to the chemical solution may be measured. In an embodiment, the taking of such a measurement, which is commonly referred to as titration, is be manually performed by a field person as described above. Optimal times for titration may be determined by any number of various types of test conditions associated with the chemical solution, the chemical product and/or operations being performed by the warewashing machine 100 over the course of one or more wash cycles.

Exemplary test conditions relate to, without limitation, the sensed concentration level of a particular chemical product relative to the chemical solution, the relationship of the sensed concentration level to the desired setpoint value for that chemical product, whether the rinse module 102 is currently dispensing water or other rinse agents, whether chemical product is being dispensed from the product reservoir 110 and whether the wash module 106 is currently dispensing the chemical solution. The aforementioned list of test conditions are exemplary only and not intended to be an exclusive list for determining the optimal time for titration. Rather, the listed test conditions are provided as an illustration of an embodiment of the present invention. The optimal time for titration is dependent on any number of factors, including, without limitation, the chemical solution being tested, but the particular utility device forming, preparing, allocating or otherwise utilizing the chemical solution. Moreover, the optimal time for titration may be based either on a single test condition or a plurality of test conditions.

After the one or more predetermined test conditions are applied to the warewash operating environment, the operation flow passes to a test query operation 308. The test query operation 308 examines the one or more predetermined test conditions to determine whether the one or more predetermined test conditions are satisfied. If the test conditions are satisfied, the operation flow passes from the test query operation 308 to an indicate operation 310.

The indicate operation 310 indicates to the field person that the current time period is an optimal time for titration. The indicate operation 310 provides such an indication by activating one or more operator perceptible indicia, such as, without limitation, an audio message or sound, a visual indicator, or a tactile indicator. In an embodiment, such an indication includes generating an icon on the graphical user interface 122, such as the titration icon 126. In this embodiment, the control module of the control box 112 performs the indicate operation 310 by generating and displaying the titration icon 126. In another embodiment, the indication may include generating a light on one or both of the status indicators 124 and/or 125. From the indication operation 310, the operation flow concludes at the termination operation 312. If the test query operation 308 determines that the one or more predetermined test conditions are not satisfied, the operation flow passes back to the application operation 306, where the operation flow continues as previously described until satisfaction of each of the one or more predetermined test conditions.

Figure 4:
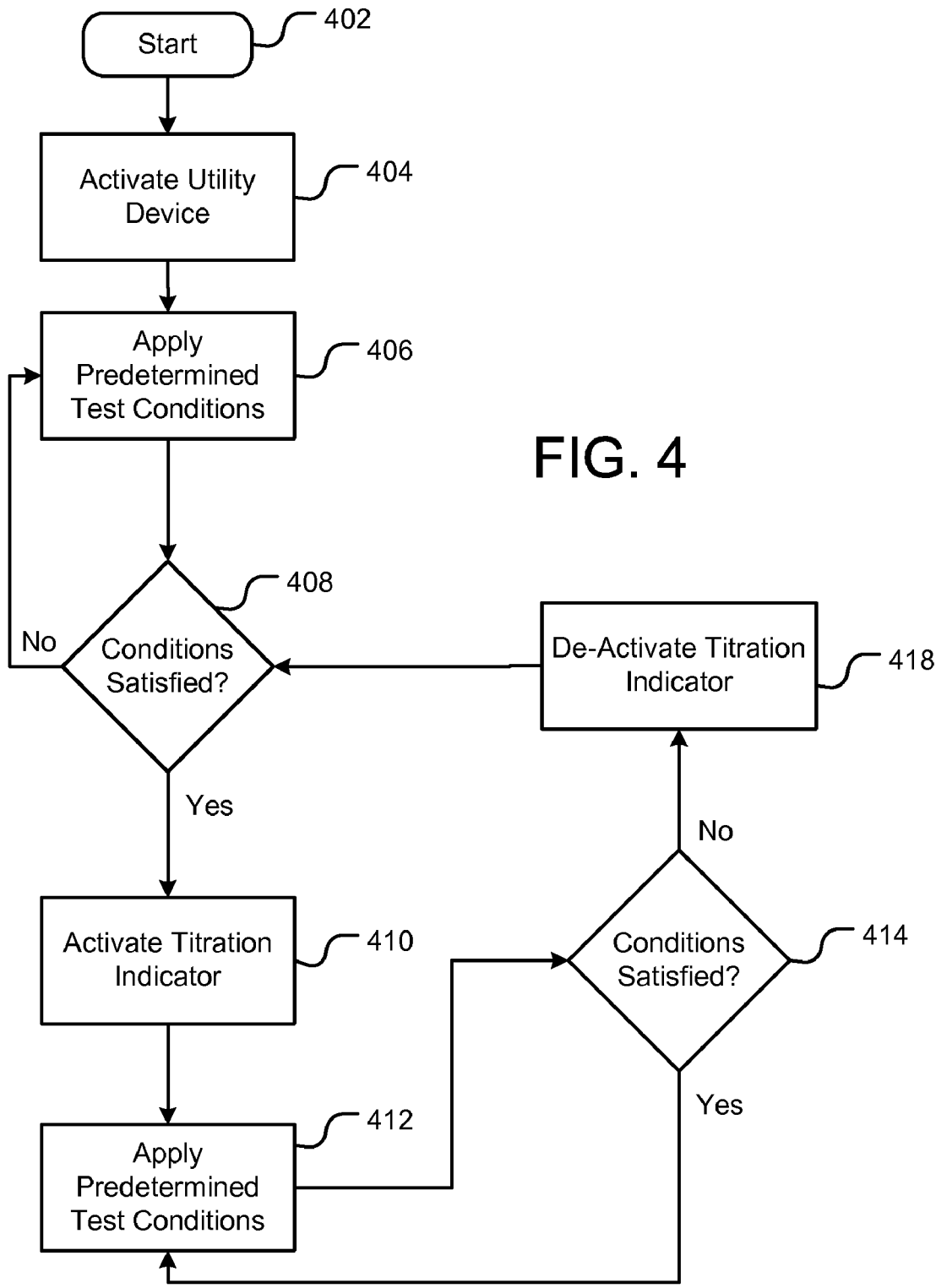
FIG. 4 is a flow diagram that illustrates operational characteristics for indicating multiple time periods for measuring percent concentration of a chemical product relative to a chemical solution in accordance with an embodiment of the present invention.

Referring now to FIG. 4, a process 400 for indicating multiple time periods optimal for measuring percent (%) concentration of a chemical product relative to a chemical solution is shown in accordance with an embodiment of the present invention. In this embodiment, the indication process 400 illustrates continuous performances of the indication process 300 shown in FIG. 3. Like FIG. 3, the indication process 400 is described below in context of a chemical solution being formed and utilized by a warewashing machine 100. The warewashing machine 100 utilizes the chemical solution to clean and sanitize articles provided to the machine 100 in an article rack 104. It should be appreciated that the present invention is not limited to application of warewashing machines 100, but rather the utility device may be any type of apparatus that prepares, formulates, allocates or otherwise utilizes a chemical solution to perform a task.

The indication process 400, which in an embodiment of FIG. 1, is performed by the control module of the control box 112, includes an operation flow that begins with a start operation 402 and continues over the operational life of the warewashing machine 100 at a particular location, such as, without limitation, a restaurant, a cafeteria or a bakery. The start operation 402 is initiated as the warewashing machine 100 is initially powered on for use at the particular location. From the start operation 402, the operation flow passes to an activate operation 404. The activate operation 404 initiates warewashing processes, which include, without limitation, applying a chemical solution to racks 104 provided to the washing chamber 108 and applying water or other rinse agents to the racks 104 following the application of chemical solution. Once initiated, the warewashing processes are performed for multiple wash cycles being applied to multiple article racks 104. After the warewashing machine 100 has activated warewashing processes, the operation flow passes to a first application operation 406.

The first application operation 406 applies one or more predetermined test conditions to the warewash operating environment, which is broadly defined to encompass, without limitation, any and all operations of the warewashing machine 100, the chemical solution formed and stored in the solution tank 140 of the machine 100, and the chemical product(s) used to form the chemical solution. The one or more predetermined test conditions are used by the control module of the control box 112 to determine optimal times during which % concentration of a particular chemical product relative to the chemical solution may be measured. In an embodiment, the taking of such a measurement, which is commonly referred to as titration, is be manually performed by a field person as described above. Optimal times for titration may be determined by any number of various types of test conditions associated with the chemical solution, the chemical product and/or operations being performed by the warewashing machine 100 over the course of one or more wash cycles. Exemplary test conditions are provided above with respect to the indication process 300 shown in FIG. 3., and therefore are not duplicated for the indication process 400 shown in FIG. 4. From the first application operation 406, the operation flow passes to a first test query operation 408.

The first test query operation 408 examines the one or more predetermined test conditions to determine whether the one or more predetermined test conditions are satisfied. If each of the test conditions are satisfied, the operation flow passes from the first test query operation 408 to a display operation 410, which is described in the preceding paragraph. If however, the first test query operation 408 determines that the one or more predetermined test conditions are not satisfied, the operation flow passes back to the first application operation 406, thereby setting up a substantially continuous loop between the first test query operation 408 and the first application operation 406 until a time period during which the one or more predetermined test conditions are satisfied.

The display operation 410 indicates to the field person that the current time period is an optimal time for titration. In an embodiment, such an indication includes generating an icon on the graphical user interface 122, such as the titration icon 126. In this embodiment, the control module of the control box 112 performs the display operation 410 by generating and displaying the titration icon 126. In accordance with an alternative embodiment, an indication that the current time period is optimal is displayed on either the first or second status indicators 124 and 125. From the display operation 410, the operation flow passes to a second application operation 412 as the indication for the optimal time for titration remains active, i.e., displayed.

The second application operation 412 repeats the operations performed by the first application operation 406 and therefore applies the one or more predetermined test conditions to the warewash environment. From the second application operation 412, the operation flow passes to a second test query operation 414. The second test query operation 414 examines the one or more predetermined test conditions to determine whether the one or more predetermined test conditions remain satisfied. If at least one of the test conditions is not satisfied, the operation flow passes from the second test query operation 414 to a deactivate operation 418, which is described in the preceding paragraph. If, however, the second test query operation 414 determines that each of the one or more predetermined test conditions remained satisfied, the operation flow passes back to the second application operation 412, thereby setting up a substantially continuous loop between the second test query operation 414 and the second application operation 412 until at least one of the predetermined test conditions fail to remain satisfied.

The deactivate operation 418 terminates indication that the current time period is an optimal time for titration. In an embodiment, the deactivate operation 418 erases the titration indicator icon from the display presented on the graphical user interface 122. In an alternative embodiment, the deactivate operation 418 terminates display of either the first or second status indicators 124 or 125, whichever was being used to indicate the occurrence of an optimal time for titration. From the deactivate operation 418, the operation flow passes to the first test query operation 408 and continues as previously described.

Referring now to FIG. 5, a process 500 for indicating an optimal time for measuring conductivity in a chemical solution is shown in accordance with an embodiment of the present invention. The indication process 500 shown in FIG. 5 illustrates the operations of the indication process 300 in more detail in accordance with this embodiment. Specifically, the indication process 500 shown in FIG. 5 illustrates in more detail application of test conditions to a warewash operating environment associated with a warewashing machine 100 that forms and stores a chemical solution in a solution tank 140. The warewash operating environment is broadly defined herein to encompass, without limitation, any and all operations of the warewashing machine 100, the chemical solution formed and stored in the solution tank 140 of the machine 100, and the chemical product(s) used to form the chemical solution.

The indication process 500, which, in an embodiment of FIG. 1, is performed by the software module of the control box 112, includes an operation flow that begins with a start operation 502 and concludes with a terminate operation 528. As with FIG. 3, an exemplary indication process 500 is shown and described in FIG. 5 as a single iteration of operations. However, it should be appreciated that the various operations of the indication process 500 are, in an embodiment, sequentially performed as part of a continuous process.

The start operation 502 is initiated as the warewashing machine 100 is activated to apply warewashing processes to one or more article racks 104 being provided to the washing chamber 108. Each instance that a rack 104 is provided to the washing chamber 108 constitutes a "wash cycle." The start operation 502 is initiated as the warewashing machine 100 is turned on to await the occurrence of an initial wash cycle. The occurrence of each wash cycle is detected as both the entry sliding door 114 and the exit sliding door 116 are closed to contain the washing chamber 108 on all sides. At such a detection of the initial wash cycle, the operation flow passes to a define setpoint operation 504.

The define setpoint operation 504 sets the conductivity setpoint value for a particular chemical product of the chemical solution formed and stored in the solution tank 140. For illustrative purposes, this particular chemical product is hereinafter referred to as the "test chemical product." In an embodiment, the conductivity setpoint value is defined herein as a user-defined concentration level for the test chemical product relative to the chemical solution. Although the concentration level is expressed herein as a percentage of the test chemical product relative to the chemical solution, the concentration level may also be defined as a particular volume of the test chemical product in the chemical solution.

In an embodiment, the conductivity setpoint value is defined by a field person responsible for titrating the chemical solution. During titration, the field person tests the chemical solution to determine whether the % concentration of the test chemical product relative to the chemical solution is equal to, or at least within a given range of, the defined setpoint value. If the actual % concentration is not equal to, or within the given range, the field person may assume that the warewashing machine 100 is not operating properly, e.g., the articles provided to the warewashing machine 100 for cleaning are not being properly cleaned and/or sanitized. As described above with reference to FIG. 1, the field person may define the conductivity setpoint value based upon selection of the value through the graphical user interface 122. From the define setpoint operation 504, the operation flow passes to an activate operation 506.

The activate operation 506 initiates warewashing processes, which include, without limitation, applying the chemical solution to racks 104 provided to the washing chamber 108 and applying water or other rinse agents to the racks 104 following application of chemical solution. Once initiated, the warewashing processes are performed for multiple wash cycles being applied to multiple article racks 104. After the warewashing machine 100 has activated warewashing processes, the operation flow passes to a first measure operation 508.

The first measure operation 508 determines the current % concentration of the test chemical product relative to the chemical solution. In an embodiment, the current % concentration rendered by the first measure operation 508 is the highest % concentration of a predetermined number of samples over a predetermined period of time. For example, the first measure operation 508 may be programmed to take ten measurements per second, wherein the highest of the ten measurements is the current % concentration measurement rendered by the first measure operation 508. In the embodiment shown in FIG. 1, the first measure operation 508 is performed by the control module of the control box 112 as sensed information is received from the one or more conductivity cells 128. The sensing of conductivity information using conductivity cells as well as use of such information to determine % concentration of a chemical product relative to a chemical solution is well known in the art, and therefore not described in further detail herein. From the first measure operation 508, the operation flow passes to a first query operation 510.

The first query operation 510 compares the current % concentration determined by the first measure operation 508 to the setpoint value defined by the define setpoint operation 504 to determine whether the % concentration is greater than or equal to a threshold percentage ($\%_{TH}$) of the defined setpoint value. In an embodiment, the threshold percentage is greater than 100% of the defined setpoint value. If the current % concentration is less than the threshold percentage, the first query operation 510 passes the operation flow to a dispense operation 512. The dispense operation 512 dispenses a predetermined volume of the test chemical product into the solution tank 140. In an embodiment, this predetermined volume, which may vary between different chemical products, is set by the field person servicing the machine 100. Various factors, including, without limitation, the defined setpoint value, may be used to determine the volume of a given chemical product dispensed by the dispense operation 512. From the dispense operation 512, the operation flow passes to the first measure operation 508 and continues as previously described until the % concentration of the test chemical product is greater than or equal to the threshold percentage.

The first query operation 510 passes the operation flow to a second query operation 514 upon a determination that the current % concentration of the test chemical product is greater than or equal to the threshold percentage. As such, the test condition of whether the current % concentration of the test chemical product is greater than or equal to the threshold percentage is satisfied. It should be appreciated to one of ordinary skill in the art that this, and all other possible test conditions used by the indication process 500, may be marked or flagged in some fashion to indicate that the condition is satisfied. Such a flag or marking is inherent in passage of the operation flow upon satisfaction of the condition.

The second query operation 514 determines whether the % concentration of the test chemical product has decreased since the previous measurement. The second query operation 514 passes the operation flow to a second measure operation 516 if it is determined that the % concentration of the test chemical product has not decreased since the previous measurement. Also, in circumstances where the operation flow performs the second query operation 514 after the initial conductivity measurement, there will be no previous measurement to which the current measurement may be compared, and thus the second query operation 514 passes directly to the second measure operation 516.

The second measure operation 516 determines a current % concentration of the test chemical product relative to the chemical solution. The second measure operation 516 is substantially identical in function and operation to the first measure operation 508, and therefore not described in further detail herein. After the second measure operation 516 determines a current % concentration, the operation flow passes back to the second query operation 514. Again, the second query operation 514 determines whether the % concentration of the test chemical product has decreased since the previous measurement. The operation flow continues passing between the second query operation 514 and the second measure operation 516 until it is determined that the % concentration has decreased from the previous reading.

The second query operation 514 passes the operation flow to a third query operation 518 upon a determination that the % concentration of the test chemical product has decreased since the previous measurement. The third query operation 514 compares the current % concentration to the defined setpoint value to determine whether the % concentration is less than or equal to the threshold percent of the defined setpoint value. If the current % concentration is greater than the threshold percentage, the third query operation 518 passes the operation flow back to the second measure operation 516 and continues as previously described. The operation flow then continues to pass between the third query operation 518, the second measure operation 516 and the second query operation 514 until the third query operation 518 determines that the current % concentration is less than or equal to the threshold percentage.

The third query operation 518 passes the operation flow to a fourth query operation 520 upon a determination that the % concentration of the test chemical product relative to the chemical solution is less than or equal to the threshold percentage. The fourth query operation 520 determines whether the rinse module 102 is currently dispensing water or other rinse agents. The period of time that the rinse module 102 is dispensing water or other rinse agents is referred to as a "rinse cycle." If the warewashing machine 100 is currently not performing a rinse cycle, the fourth query operation 520 passes the operation flow to a sixth query operation 522.

The sixth query operation 522 determines whether the warewashing machine 100 is currently performing a wash cycle. If the warewashing machine 100 is currently performing a wash cycle, the sixth query operation 522 passes the operation flow to a display operation 526. The display operation 526 indicates to the field person that the current time period is an optimal time for titration. In an embodiment, such an indication includes generating an icon on the graphical user interface 122, such as the titration icon 126. In this embodiment, the control module of the control box 112 performs the display operation 526 by generating and displaying the titration icon 126. From the display operation 526, the operation flow concludes at the terminate operation 528. If the sixth query operation 522 determines that the warewashing machine 100 is not performing a wash cycle, the operation flow is passed to a hold operation 524, which pauses the operation flow until the start of the next wash cycle. At the start of the next wash cycle, the hold operation passes the operation flow to the display operation 526.

Referring back to the fourth query operation 520, if the warewashing machine 100 is currently performing a rinse cycle, the operation flow is passed to a fifth query operation 521. The fifth query operation 521 determines whether the current % concentration of the test chemical product relative to the chemical solution is less than or equal to the defined setpoint value. If the current % concentration is less than or equal to the defined setpoint value, the fifth query operation 521 passes the operation flow back to the dispense operation 512 and continues as previously described. If, however, the current % concentration is greater than the defined setpoint value, the fifth query operation 521 passes back to the fourth query operation 520, which determines whether the warewashing machine 100 is currently in a rinse cycle. The operation flow thereafter continues passing between the fourth query operation 520 and the fifth query operation 521 until either the current % concentration is less than or equal to the defined setpoint value or the rinse cycle of the warewashing machine 100 is completed.

It will be clear that the present invention is well adapted to attain the ends and advantages mentioned, as well as those inherent therein. While a presently preferred embodiment has been described for purposes of this disclosure, various changes and modifications may be made which are well within the scope of the present invention. The indication process 500 shown in FIG. 5 may utilize any number and/or combination of the illustrated test conditions in order to determine an optimal time for titrating the chemical solution. For example, the indication process 500 may define an optimal time for titration as any time period when the conductivity is less than the threshold percentage and greater than the defined setpoint value. Also, an optimal time for titration may be defined as any time period wherein the warewashing machine 100 has completed a wash cycle and before a rinse cycle is initiated. Furthermore, the control module of the control box 112 is described herein as a processor 201, but may be replaced by or include conventional electrical and electronic devices/components, such as, without limitation, programmable logic controllers (PLC's) and logic components. In this embodiment, the sensing of information, controlling of warewash operations, application and analysis of the test conditions and display of the titration icon 126 are administered by these conventional electrical and electronic devices/components. Furthermore, the titration indicator is described as a single event, such as a display or audio sound, but may be any combination of tactile, audio or visual events operable to indicate optimal times for titrating. Numerous other changes may be made which will readily suggest themselves to those skilled in the art and which are encompassed in the spirit of the invention disclosed and as defined in the appended claims.

What is claimed is:

1. A method for indicating a time period for titrating a chemical solution contained in a solution tank of a utility device to determine whether the chemical solution contains a desired concentration of a chemical product, the method comprising:
measuring a current concentration of the chemical product in the chemical solution;
determining whether the current concentration satisfies one of one or more test conditions indicative of the time period for titrating the chemical solution; and
if each of the one or more test conditions is satisfied, displaying a titration indicator indicative of the time period for titrating the chemical solution on a display device.

2. The method of claim 1, wherein displaying a titration indicator comprises:
generating an icon representing the titration indicator; and
displaying the icon on a graphical user interface.

3. The method of claim 1, wherein displaying a titration indicator comprises supplying a current through a light emitting diode (LED).

4. The method of claim 1, wherein displaying a titration indicator comprises activating a plurality of operator perceptible indicia.

5. The method of claim 4, wherein activating a plurality of operator perceptible indicia comprises activating an audio event and a visual event.

6. The method of claim 1, further comprising defining a setpoint value associated with the desired concentration of the chemical product in the chemical solution.

7. The method of claim 6, wherein defining a setpoint value comprises:
presenting a list of possible setpoint values on a graphical user interface; and
receiving, via the graphical user interface, a selection of the setpoint value from among the list of possible setpoint values.

8. The method of claim 6, wherein determining whether the current concentration satisfies one of the one or more test conditions indicative of the time period for titrating the chemical solution comprises: comparing the current concentration of the chemical product to a threshold percentage of the setpoint value.

9. The method of claim 6, further comprising:
determining, based on control signals associated with a chemical product dispenser, whether or not the chemical product is being dispensed into the solution tank; and displaying a titration indicator indicative of the time period for titrating the chemical solution on a display device if the current concentration of the chemical product is less than a threshold percentage of the setpoint value and the chemical product is not being dispensed into the solution tank.

10. The method of claim 9, wherein the utility device is connected to a product reservoir for storing the chemical product and dispensing the chemical product to the solution tank, and wherein detecting whether the chemical product is being dispensed comprises receiving information from the product reservoir indicating whether the chemical product is being dispensed into the solution tank.

11. The method of claim 6, further comprising:
determining, based on control signals associated with a chemical product dispenser, whether or not the chemical product is being dispensed into the solution tank;
determining, based on control signals associated with a rinse module, whether or not a rinse agent is being applied to the one or more articles; and
displaying a titration indicator indicative of the time period for titrating the chemical solution on a display device if the current concentration of the chemical product is less than a threshold percentage of the setpoint value, the rinse agent is not being applied to the one or more articles and the chemical product is not being dispensed into the solution tank.

12. The method of claim 6, further comprising:
detecting whether the utility device is performing a wash cycle;
determining, based on control signals associated with a chemical product dispenser, whether or not the chemical product is being dispensed into the solution tank;
determining, based on control signals associated with a rinse module, whether or not a rinse agent is being applied to the one or more articles; and
displaying a titration indicator indicative of the time period for titrating the chemical solution on a display device if the current concentration of the chemical product is less than a threshold percentage of the setpoint value, the rinse agent is not being applied to the one or more articles, the chemical product is not being dispensed into the solution tank and the utility device is performing a wash cycle.

13. The method of claim 1, wherein measuring the current concentration of the chemical product in the solution comprises measuring the current concentration of the chemical product using one or more conductivity cells located within the solution tank.

14. The method of claim 1, wherein the utility device is a warewashing machine.

15. The method of claim 1, wherein the chemical product includes a detergent and the rinse agent includes water.

* * * * *